(12) United States Patent
Müller et al.

(10) Patent No.: US 7,186,834 B2
(45) Date of Patent: Mar. 6, 2007

(54) SUBSTITUTED IMINOAZINES

(75) Inventors: Klaus-Helmut Müller, Düsseldorf (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 555 days.

(21) Appl. No.: 10/276,867

(22) PCT Filed: May 8, 2001

(86) PCT No.: PCT/EP01/05203

§ 371 (c)(1),
(2), (4) Date: Nov. 15, 2002

(87) PCT Pub. No.: WO01/90071

PCT Pub. Date: Nov. 29, 2001

(65) Prior Publication Data

US 2004/0029881 A1 Feb. 12, 2004

(30) Foreign Application Priority Data

May 19, 2000 (DE) .............................. 100 24 938

(51) Int. Cl.
C07D 213/00 (2006.01)
C07D 211/72 (2006.01)
C07D 251/00 (2006.01)
C07D 237/02 (2006.01)

(52) U.S. Cl. .............................. 546/1; 546/304; 544/1; 544/180; 544/224; 544/242

(58) Field of Classification Search .................... 546/1, 546/304; 544/1, 180, 224, 242
See application file for complete search history.

(56) References Cited

U.S. PATENT DOCUMENTS

| 3,503,986 A | 3/1970 | Seidel et al. ............. 260/294.9 |
| 3,697,522 A | 10/1972 | Reicheneder et al. ... 260/250 A |
| 3,761,240 A | 9/1973 | Seidel et al. .................... 71/76 |
| 3,839,346 A | 10/1974 | Gadekar ................. 260/297 Z |
| 3,974,281 A | 8/1976 | Gadekar ..................... 424/263 |
| 4,042,699 A | 8/1977 | Gadekar ..................... 424/263 |
| 4,052,509 A | 10/1977 | Gadekar ..................... 424/263 |

FOREIGN PATENT DOCUMENTS

| DE | 22 32 964 | 2/1974 |
| EP | 0 432 600 | 6/1991 |
| WO | WO 98/00408 | * 1/1998 |

OTHER PUBLICATIONS

Chem. Pharm. Bull. 45(4), (month unavailable) 1997, pp. 719-721, Masakatsu Sugahara and Tatsuzo Ukita, "A Facile Copper-Catalyzed Ullmann Condensation: N-Arylation of Heterocyclic Compounds Containing an—NHCO- Moiety".

*Database CA [Online] Chemical Abstracts Service, Columbus, Ohio, US; Konecny, V. et al: "Synthesis, spectral properties, and pesticidal activity of 4,5-dichloro-2-R-3-oxo-2H-pyridazines" retrieved from STN Database accession No. 101:110848 XP002177756 CAS RN 26806-47-3; 41931-11-7; 41931-13-9 Zusammenfassung & Chem. Zvesti, Bd. 38, Nr. 2, 1984, Seiten 239-246, ISSN: 0366-6352.

*Database CA [Online] Chemical Abstracts Service, Columbus, Ohio, US; Boberg, Friedrich et al: "Reaction of thioxoheterocycles with N-chloroamides. II. N-substituted 2 or 4-thiopyridone and sodium N-chlorobenzenesulfonamide" retrieved from STN Database accession No. 112:216635 XP002177757 CAS RN 126957-93-5; 126957-94-5; 126957-94-6; 126957-95-7 Zusammenfassung & Phosphorus, Sulfur Silicon Relat. Elem., Bd. 44, Nr. 3-4, 1989, Seiten 267-284, ISSN: 1042-6507.

*Database CA [Online] Chemical Abstracts Service, Columbus, Ohio, US; Plukse, I. et al: "Delta.. Alpha.,.beta.-Butenolides. XII. Syntheses based on 2,4-pentadienoic acid derivatives" retrieved from STN Database accession No. 107:77578 XP002177758 CAS RN 109753-91-5; 109753-85-7; 109754-01-0 Zusammenfassung & Latv. PSR Zinat. Akad. Vestis, Kim. Ser., Nr. 4, 1986, Seiten 471-478, ISSN: 0002-3248.

*Meth-Cohn, Otto et al: A versatile new synthesis of quinolines and related fused pyridines. Par 11. Conversion of acylanilides into. alpha.-aminopyridines: Journal of the Chemical Society, Perkin Transactions 1., Nr. 9, 1983, Seiten 2089-2092, XP002177755 Chemical Society. Letchworth., GB ISSN: 1472-7781 Tabelle 2.

* cited by examiner

*Primary Examiner*—James O. Wilson
*Assistant Examiner*—Paul V. Ward
(74) *Attorney, Agent, or Firm*—Richard E. L. Henderson

(57) ABSTRACT

The invention relates to novel substituted iminoazines of the general formula (I)

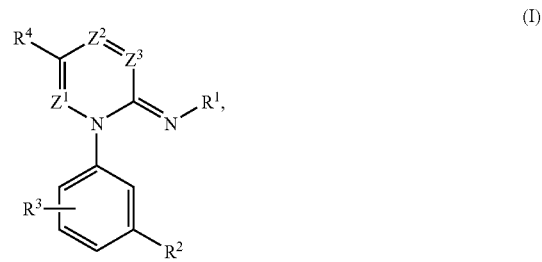

in which $R^1$, $R^2$, $R^3$, $R^4$, $Z^1$, $Z^2$ and $Z^3$ are each as defined in the disclosure,
to a plurality of processes for their preparation, and to their use as herbicides.

10 Claims, No Drawings

SUBSTITUTED IMINOAZINES

The present patent application has been filed under 35 U.S.C. 371 as a national stage application of International Application No. PCT/EP01/05203, filed May 8, 2001, which was published in German as International Patent Publication WO 01/90071 on Nov. 29, 2001, which is entitled to the right of priority of German Patent Application No. 100 24 938.8, filed May 19, 2000.

The invention relates to novel substituted iminoazines, to processes for their preparation and to their use as plant treatment agents, in particular as herbicides.

It is already known that certain substituted iminopyridines have herbicidal properties (cf. EP-A-432 600). However, the activity of these compounds is not entirely satisfactory.

This invention, accordingly, provides the novel substituted aminoazines of the general formula (I)

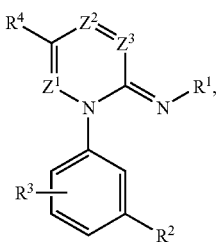

in which
$R^1$ represents nitro, cyano or one of the groupings —$R^5$, —$CQ^1$-$Q^2$-$R^5$, —NH—$CQ^1$-$Q^2$-$R^5$ or —$SO_2$—$R^6$,
$R^2$ represents nitro, cyano, $SF_5$, halogen or in each case optionally substituted alkyl, alkoxy, alkylthio, alkylsulphinyl, alkylsulphonyl or alkylsulphonyloxy,
$R^3$ represents hydrogen or halogen, or together with $R^2$ represents optionally substituted alkylenedioxy,
$R^4$ represents hydrogen, cyano, carboxyl, carbamoyl, halogen or optionally substituted alkyl,
$Q^1$ represents O (oxygen), S (sulphur) or N—$R^5$,
$Q^2$ represents a single bond or represents O (oxygen), S (sulphur) or N—$R^5$,
$R^5$ represents hydrogen, amino or in each case optionally substituted alkyl, alkoxy, alkylamino, dialkylamino, alkylideneamino, alkenyl, alkenyloxy, alkinyl, cycloalkyl, cycloalkylamino, cycloalkylalkyl, aryl, arylamino, arylalkyl, heterocyclyl or heterocyclylalkyl,
$R^6$ represents in each case optionally substituted alkyl, alkenyl, cycloalkyl, cycloalkylalkyl, aryl, arylalkyl, heterocyclyl or heterocyclylalkyl,
$Z^1$ represents N (nitrogen) or C—$R^4$,
$Z^2$ represents N (nitrogen) or C—$R^4$, and
$Z^3$ represents N (nitrogen) or C—$R^4$.

In the definitions, the hydrocarbon chains, such as alkyl, alkenyl or alkinyl, are in each case straight-chain or branched—including in combination with heteroatoms, such as in alkylamino. $R^3$ is preferably located in the meta or para position on the phenyl ring.

Preferred substituents or preferred ranges of the radicals which are present in the formulae listed above and below are defined below.

$R^1$ preferably represents cyano or one of the groupings —$R^5$, —$CQ^1$-$Q^2$-$R^5$, —NH—$CQ^1$-$Q^2$-$R^5$ or —$SO_2$—$R^6$.
$R^2$ preferably represents nitro, cyano, $SF_5$, halogen or in each case optionally cyano-, halogen- or $C_1$–$C_4$-alkoxy-substituted alkyl, alkoxy, alkylthio, alkylsulphinyl, alkylsulphonyl or alkylsulphonyloxy having in each case 1 to 5 carbon atoms.
$R^3$ preferably represents hydrogen or halogen, or together with $R^2$ represents optionally halogen-substituted alkylenedioxy having 1 to 3 carbon atoms.
$R^4$ preferably represents hydrogen, cyano, carboxyl, carbamoyl, halogen or optionally cyano-, halogen- or $C_1$–$C_4$-alkoxy-substituted alkyl having 1 to 5 carbon atoms.
$Q^1$ preferably represents O (oxygen) or S (sulphur).
$R^5$ preferably represents hydrogen or amino, represents in each case optionally cyano-, halogen- or $C_1$–$C_4$-alkoxy-substituted alkyl or alkoxy having in each case 1 to 6 carbon atoms, represents alkylamino having 1 to 6 carbon atoms, represents dialkylamino having in each case 1 to 6 carbon atoms in the alkyl groups, represents alkylideneamino having up to 6 carbon atoms, represents in each case optionally cyano- or halogen-substituted alkenyl, alkenyloxy or alkinyl having in each case 2 to 6 carbon atoms, represents in each case optionally cyano-, halogen- or $C_1$–$C_4$-alkyl-substituted cycloalkyl, cycloalkylamino or cycloalkylalkyl having in each case 3 to 6 carbon atoms in the cycloalkyl group and optionally 1 to 4 carbon atoms in the alkyl moiety, represents in each case optionally nitro-, cyano-, phenyl-, phenoxy-, phenylthio-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl- or di-($C_1$–$C_4$-alkyl)-aminosulphonyl-substituted aryl, arylamino or arylalkyl having in each case 6 or 10 carbon atoms in the aryl group and optionally 1 to 4 carbon atoms in the alkyl moiety, or represents in each case optionally nitro-, cyano-, phenyl-, phenoxy-, phenylthio-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl- or di-($C_1$–$C_4$-alkyl)-amino-sulphonyl-substituted monocyclic or bi-cyclic heterocyclyl or heterocyclylalkyl having in each case up to 10 carbon atoms and up to 4 nitrogen atoms and/or 1 or 2 oxygen or sulphur atoms in the heterocyclyl group and optionally 1 to 4 carbon atoms in the alkyl moiety.
$R^6$ preferably represents optionally halogen-substituted alkyl having 1 to 6 carbon atoms, represents optionally halogen-substituted alkenyl having 2 to 6 carbon atoms, represents optionally halogen- or $C_1$–$C_4$-alkyl-substituted cycloalkyl or cycloalkylalkyl having in each case 3 to 6 carbon atoms in the cycloalkyl group and optionally 1 to 4 carbon atoms in the alkyl moiety, represents in each case optionally nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl- or di-($C_1$–$C_4$-alkyl)-amino-sulphonyl-substituted aryl or arylalkyl having in each case 6 or 10 carbon atoms in the aryl group and optionally 1 to 4 carbon atoms in the alkyl moiety, or represents in each case optionally nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl- or di-($C_1$–$C_4$-alkyl)-amino-sulphonyl-substituted monocyclic or bicyclic heterocyclyl or heterocyclylalkyl having in each case up to 10 carbon atoms and up to 4 nitrogen atoms and/or 1 or 2 oxygen or sulphur atoms in the heterocyclyl group and optionally 1 to 4 carbon atoms in the alkyl moiety.

$Z^1$ preferably represents C—$R^4$.

$Z^2$ preferably represents C—$R^4$.

$Z^3$ preferably represents C—$R^4$.

$R^2$ particularly preferably represents nitro, cyano, $SF_5$, fluorine, chlorine or bromine, or represents in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, methylsulphonyloxy, ethylsulphonyloxy, n- or i-propylsulphonyloxy.

$R^3$ particularly preferably represents hydrogen, fluorine, chlorine or bromine, or together with $R^2$ represents in each case optionally fluorine- and/or chlorine-substituted methylenedioxy or ethylenedioxy.

$R^4$ particularly preferably represents hydrogen, cyano, carboxyl, carbamoyl, fluorine, chlorine, bromine or represents optionally cyano-, fluorine-, chlorine-, methoxy- or ethoxy-substituted methyl, ethyl, n- or i-propyl.

$Q^1$ particularly preferably represents O (oxygen).

$R^5$ particularly preferably represents hydrogen or amino, represents in each case optionally cyano-, fluorine-, chlorine-, methoxy- or ethoxy-substituted methyl, ethyl, n- or i-propyl, n-, i-, s- or t-butyl, methylamino, ethylamino, n- or i-propylamino, n-, i-, s- or t-butylamino, represents dimethylamino or diethylamino, represents propylideneamino or butylideneamino, represents in each case optionally cyano-, fluorine-, chlorine- and/or bromine-substituted propenyl, butenyl, propinyl or butinyl, represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl, represents in each case optionally nitro-, cyano-, phenyl-, phenoxy-, phenylthio-, fluorine-, chlorine-, bromine-, methyl-, ethyl-, n- or i-propyl-, n-, i-, s- or t-butyl-, dichloromethyl-, difluoromethyl-, trichloromethyl-, trifluoromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl- or dimethylaminosulphonyl-substituted phenyl, naphthyl, phenylamino, benzyl or phenylethyl, or represents in each case optionally cyano-, phenyl-, phenoxy-, phenylthio-, fluorine-, chlorine-, bromine-, methyl-, ethyl-, n- or i-propyl-, n-, i-, s- or t-butyl-, dichloromethyl-, difluoromethyl-, trichloromethyl-, trifluoromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl- or dimethylaminosulphonyl-substituted heterocyclyl or heterocyclylalkyl from the group consisting of furyl, tetrahydrofuryl, benzofuryl, thienyl, benzothienyl, pyrrolyl, benzopyrrolyl, pyrazolyl, benzopyrazolyl, oxazolyl, benzoxazolyl, isoxazolyl, thiazolyl, benzothiazolyl, oxadiazolyl, thiadiazolyl, pyridinyl, quinolinyl, pyrimidinyl, furylmethyl, thienylmethyl, pyrrolylmethyl, pyrazolylmethyl, oxazolylmethyl, thiazolylmethyl, pyridinylmethyl, pyrimidinylmethyl.

$R^6$ particularly preferably represents in each case optionally fluorine- and/or chlorine-substituted methyl, ethyl, n- or i-propyl, n-, i-, s- or t-butyl, represents in each case optionally fluorine-, chlorine- and/or bromine-substituted propenyl or butenyl, represents in each case optionally fluorine-, chlorine-, bromine-, methyl-, ethyl-, n- or i-propyl-substituted cyclopropyl, cyclobutyl, cyclopentyl, cyclohexyl, cyclopropylmethyl, cyclobutylmethyl, cyclopentylmethyl or cyclohexylmethyl, represents in each case optionally nitro-, cyano-, fluorine-, chlorine-, bromine-, methyl-, ethyl-, n- or i-propyl-, n-, i-, s- or t-butyl-, dichloromethyl-, difluoromethyl-trichloromethyl-, trifluoromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl- or dimethylaminosulphonyl-substituted phenyl or naphthyl, or represents in each case optionally cyano-, fluorine-, chlorine-, bromine-, methyl-, ethyl-, n- or i-propyl-, n-, i-, s- or t-butyl-, dichloromethyl-, difluoromethyl-, trichloromethyl-, trifluoromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl- or dimethylaminosulphonyl-substituted heterocyclyl or heterocyclylalkyl from the group consisting of furyl, benzofuryl, thienyl, benzothienyl, pyrrolyl, benzopyrrolyl, pyrazolyl, benzopyrazolyl, oxazolyl, benzoxazolyl, isoxazolyl, thiazolyl, benzothiazolyl, pyridinyl, quinolinyl, pyrimidinyl, furylmethyl, thienylmethyl, pyrrolylmethyl, pyrazolylmethyl, oxazolylmethyl, thiazolylmethyl, pyridinylmethyl, pyrimidinylmethyl.

$Z^1$ particularly preferably represents CH.

$Z^2$ particularly preferably represents CH.

$Z^3$ particularly preferably represents CH.

$R^2$ very particularly preferably represents cyano, fluorine, chlorine or bromine, or represents in each case optionally fluorine-, chlorine-, methoxy- or ethoxy-substituted methyl, ethyl, methoxy, ethoxy, methylthio, ethylthio, methylsulphinyl, ethylsulphinyl, methylsulphonyl, ethylsulphonyl, methylsulphonyloxy or ethylsulphonyloxy.

$R^4$ very particularly preferably represents hydrogen, cyano, fluorine, chlorine, bromine, or represents optionally fluorine-, chlorine-, methoxy- or ethoxy-substituted methyl or ethyl.

$R^5$ very particularly preferably represents hydrogen or amino, represents in each case optionally cyano-, fluorine-, chlorine-, methoxy- or ethoxy-substituted methyl, ethyl, n- or i-propyl, methylamino, ethylamino, n- or i-propylamino, represents dimethylamino, represents in each case optionally fluorine-, chlorine- and/or bromine-substituted propenyl, butenyl, propinyl or butinyl, represents in each case optionally fluorine-, chlorine-, bromine-, methyl- or ethyl-substituted cyclopropyl, cyclopentyl, cyclohexyl, cyclopropylamino, cyclopentylamino, cyclohexylamino, cyclopropylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl- or dimethylaminosulphonyl-substituted phenyl, phenylamino, benzyl or phenylethyl.

$R^6$ very particularly preferably represents in each case optionally fluorine- and/or chlorine-substituted methyl, ethyl, n- or i-propyl, n-, i-, s- or t-butyl, represents in each case optionally fluorine-, chlorine-, bromine-, methyl- or ethyl-substituted cyclopropyl, cyclopentyl or cyclohexyl, or represents optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl- or dimethylaminosulphonyl-substituted phenyl.

$R^2$ most preferably represents trifluoromethyl.

$R^4$ most preferably represents methyl.

A very particularly preferred group are those compounds of the formula (I) in which $R^1$ represents cyano or one of the groupings —$CQ^1$-$Q^2$-$R^5$ or —$SO_2$—$R^6$, $R^2$ represents trifluoromethyl, difluoromethoxy or trifluoromethoxy, $R^3$ represents hydrogen, fluorine or chlorine, or together with $R^2$—in the ortho position—represents difluoromethylenedioxy or tetrafluoroethylenedioxy, $R^4$ represents hydrogen, fluorine, chlorine, bromine or methyl, $Q^1$ represents O (oxygen) or S (sulphur), $Q^2$ represents a single bond or represents O (oxygen), S (sulphur) or N—$R^5$, $R^5$ represents hydrogen, represents in each case optionally cyano-, fluorine-, chlorine-, methoxy- or ethoxy-substituted methyl, ethyl, n- or i-propyl, represents in each case optionally fluorine-, chlorine- and/or bromine-substituted propenyl, butenyl, propinyl or butinyl, represents in each case optionally fluorine-, chlorine- or methyl-substituted cyclopropyl, cyclopentyl, cyclohexyl, cyclopropylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl- or dimethylaminosulphonyl-substituted phenyl or benzyl, $R^6$ represents in each case optionally fluorine-, and/or chlorine-substituted methyl, ethyl, n- or i-propyl, n-, i-, s- or t-butyl, represents in each case optionally fluorine-, chlorine- or methyl-substituted cyclopropyl, cyclopentyl or cyclohexyl, or represents optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl- or dimethylaminosulphonyl-substituted phenyl, $Z^1$ represents CH, $Z^2$ represents CH, and $Z^3$ represents CH.

Preference according to the invention is given to those compounds of the formula (I) which contain a combination of the meanings listed above as being preferred.

Particular preference according to the invention is given to those compounds of the formula (I) which contain a combination of the meanings given above as being particularly preferred.

Very particular preference according to the invention is given to those compounds of the formula (I) which contain a combination of the meanings given above as being very particularly preferred.

The general or preferred radical definitions listed above apply both to the end products of the formula (I) and, correspondingly, to the starting materials or intermediates required in each case for the preparation.

These radical definitions can be combined with one another as desired, i.e. including combinations between the given preferred ranges.

The novel substituted iminoazines of the general formula (I) have interesting biological properties. In particular, they have strong herbicidal activity.

The novel substituted iminoazines of the general formula (I) are obtained when (a) iminoazines of the general formula (II)

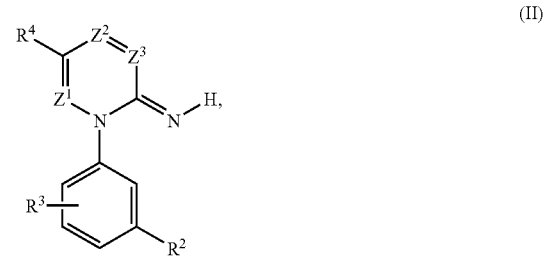

(II)

in which $R^2$, $R^3$, $R^4$, $Z^1$, $Z^2$ and $Z^3$ are each as defined above or acid adducts of iminoazines of the general formula (II), —such as, for example, the hydrochlorides are reacted with compounds of the general formula (III)

$$X^1—R^1 \quad (III)$$

in which $R^1$ is as defined above, $X^1$ represents halogen, —$SO_2CH_3$, —O—CO—$R^5$ or —O—$SO^2$—$R^6$ and $R^5$ and $R^6$ are each as defined above, or with iso(thio)cyanates of the general formula (IV)

$$Q^1=C=N—R^5 \quad (IV)$$

in which $Q^1$ and $R^5$ are each as defined above, if appropriate in the presence of a reaction auxiliary and if appropriate in the presence of a diluent, or when (b) azinethiones of the general formula (V)

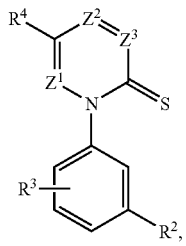

(V)

in which
R$^2$, R$^3$, R$^4$, Z$^1$, Z$^2$ and Z$^3$ are each as defined above are reacted with compounds of the general formula (VI)

M$^+$Cl$^-$N—SO$_2$—R$^6$      (VI)

in which
R$^6$ is as defined above and
M represents a metal equivalent,
if appropriate in the presence of one or more diluents, or when
(c) chloroazinium compounds of the general formula (VII)

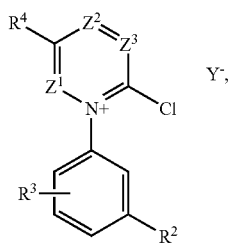

(VII)

in which
R$^2$, R$^3$, R$^4$, Z$^1$, Z$^2$ and Z$^3$ are each as defined above, and Y represents Cl, PCl$_4$, POCl$_4$ or PCl$_6$ are reacted with amino compounds of the general formula (VIII)

H$_2$N—R$^1$      (VIII)

in which
R$^1$ is as defined above,
if appropriate in the presence of a reaction auxiliary and if appropriate in the presence of a diluent,
or when
(d) iminoazines of the general formula (II)

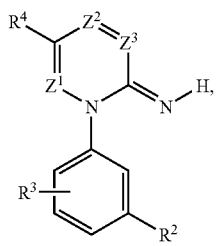

(II)

in which
R$^2$, R$^3$, R$^4$, Z$^1$, Z$^2$ and Z$^3$ are each as defined above
or acid adducts of iminoazines of the general formula (II), such as, for example, the hydrochlorides
are reacted with nitric acid, if appropriate in the presence of a reaction auxiliary and/or diluent.

Using, for example, 5-chloro-1-(3-cyano-phenyl)-2(1H)-pyridineimine and acetyl chloride as starting materials, the course of the reaction in the process (a) according to the invention can be illustrated by the following formula scheme:

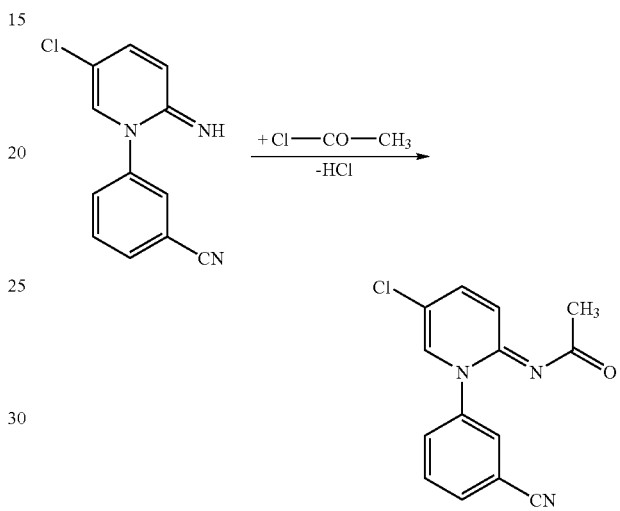

Using, for example, 1-(3-chloro-phenyl)-5-ethyl-2(1H)-pyridinethione and N-chlorobenzenesulphonamide sodium salt as starting materials, the course of the reaction in the process (b) according to the invention can be illustrated by the following formula scheme:

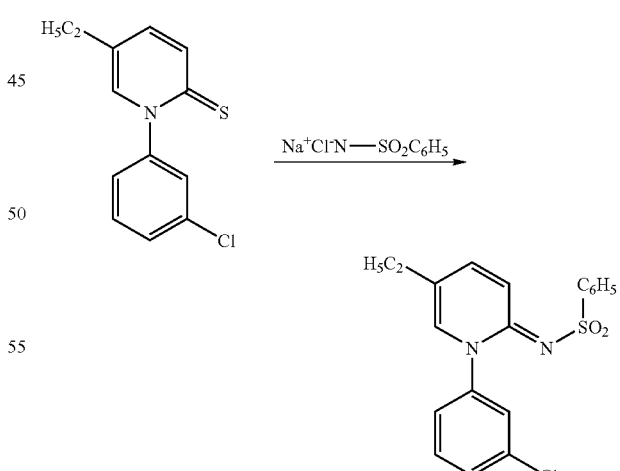

Using, for example, 1-(3-bromo-phenyl)-2-chloro-5-trifluoromethyl-pyridinium chloride and dimethylhydrazine as starting materials, the course of the reaction in the process (c) according to the invention can be illustrated by the following formula scheme:

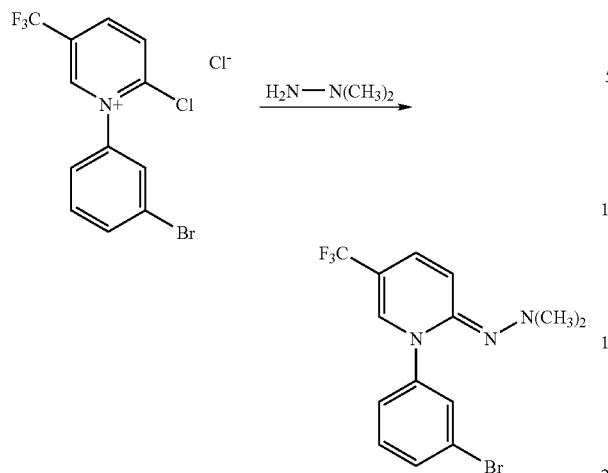

Using, for example, 5-bromo-1-(3-chlorodifluoromethyl-phenyl)-2(1H)-pyridineimine and nitric acid as starting materials, the course of the reaction in the process (d) according to the invention can be illustrated by the following formula scheme:

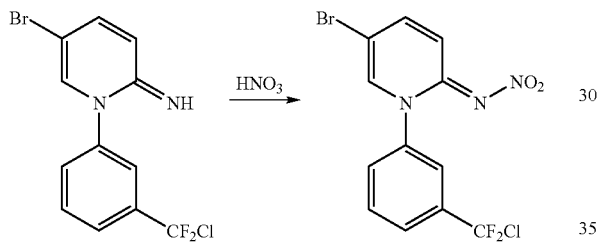

The formula (II) provides a general definition of the iminoazines to be used as starting materials in the processes (a) and (d) according to the invention for preparing compounds of the general formula (I). In the general formula (II), $R^2$, $R^3$, $R^4$, $Z^1$, $Z^2$ and $Z^3$ each preferably have those meanings which have already been mentioned above, in connection with the description of the compounds of the general formula (I) according to the invention, as being preferred, particularly preferred or very particularly preferred for $R^2$, $R^3$, $R^4$, $Z^1$, $Z^2$ and $Z^3$.

The starting materials of the general formula (II) have hitherto not been disclosed in the literature; as novel substances, they also form part of the subject-matter of the present application.

The novel iminoazines of the general formula (II), are obtained when (α) azinones of the general formula (IX)

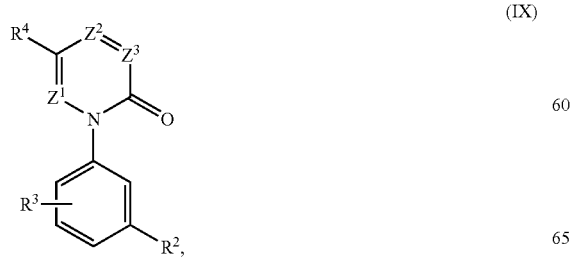

in which $R^2$, $R^3$, $R^4$, $Z^1$, $Z^2$ and $Z^3$ are each as defined above are reacted, in a first step, with chlorinating agents, such as, for example, phosgene, diphosgene, oxalyl chloride, thionyl chloride, phosphorus(III) chloride, phosphoryl chloride or phosphorus(V) chloride, if appropriate in the presence of reaction auxiliaries, such as, for example, N,N-dimethyl-formamide, and if appropriate in the presence of diluents, such as, for example, 1,2-dichloro-ethane, at temperatures between 0° C. and 150° C. (cf. the Preparation Examples)

and the resulting chloroazinium compounds of the general formula (VII)

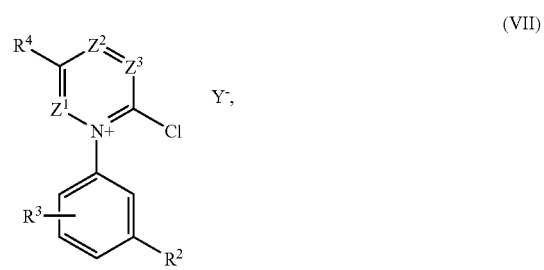

in which $R^2$, $R^3$, $R^4$, $Z^1$, $Z^2$ and $Z^3$ are each as defined above and Y represents Cl, $PCl_4$, $POCl_4$ or $PCl_6$ are, in a second step, reacted with ammonia, if appropriate in the presence of a diluent, such as, for example, methanol, and if appropriate in the presence of an acid acceptor, such as, for example, sodium methoxide, at temperatures between 0° C. and 80° C. (cf. the preparation examples), or when (β) substituted iminoazines of the general formula (Ia)

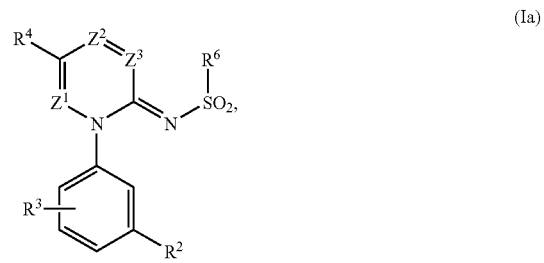

in which $R^2$, $R^3$, $R^4$, $R^6$, $Z^1$, $Z^2$ and $Z^3$ are each as defined above are reacted with a strong acid, such as, for example, sulphuric acid, which is optionally diluted with water, at temperatures between 0° C. and 100° C. (cf. the Preparation Examples).

The starting materials of the general formula (IX) are partly known and/or can be prepared by known processes (cf. Chem. Pharm. Bull. 45 (1997), 719–721, DE-A-1900947, DE-A-2362958, DE-A-2555411, cf. also the Preparation Examples).

The starting materials of the general formula (IXa)

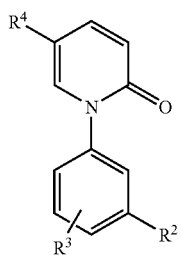

(IXa)

wherein $R^2$, $R^3$ and $R^4$ are each as defined above,
are novel compounds according to the invention for preparing compounds of the general formula (II). In the general formula (IXa), $R^2$, $R^3$ and $R^4$ each preferably have those meanings which have already been mentioned above, in connection with the description of the compounds of the general formula (I) according to the invention, as being preferred, particularly preferred or very particularly preferred for $R^2$, $R^3$ and $R^4$.

The starting materials of the general formula (IXa) have hitherto not been disclosed in the literature; as novel substances, they also form part of the subject matter of the present application.

The novel compounds of the general formula (IXa) can be prepared by known processes (cf. Chem. Pharm. Bull. 45 (1997), 719–721, DE-A-1900947, DE-A-2362958, DE-A-2555411, cf. also the Preparation Examples).

The compounds of the general formula (IX) as well as the compounds of the formula (IXa) also have interesting biological properties. In particular, they show a strong herbicidal activity.

The substituted iminoazines of the general formula (Ia) are novel compounds according to the invention; they are preferably prepared by the process (b) according to the invention.

The formulae (III) and (IV) provide general definitions of the compounds further to be used as starting materials in the process (a) according to the invention for preparing compounds of the general formula (I). In the general formulae (III) and (IV), $R^1$ preferably has that meaning which has already been mentioned above, in connection with the description of the compounds of the general formula (I) according to the invention, as being preferred, particularly preferred or very particularly preferred for $R^1$; $X^1$ preferably represents fluorine, chlorine, bromine or the grouping —O—CO—$R^1$, in particular chlorine or bromine; $Q^1$ preferably represents O or S.

The starting materials of the general formulae (III) and (IV) are known organic chemicals for synthesis.

The formula (V) provides a general definition of the azinethiones to be used as starting materials in the process (b) according to the invention for preparing compounds of the general formula (I). In the general formula (V), $R^2$, $R^3$, $R^4$, $Z^1$, $Z^2$ and $Z^3$ each preferably have those meanings which have already been mentioned above, in connection with the description of the compounds of the general formula (I) according to the invention, as being preferred, particularly preferred or very particularly preferred for $R^2$, $R^3$, $R^4$, $Z^1$, $Z^2$ and $Z^3$.

The starting materials of the general formula (V) have hitherto not been disclosed in the literature; as novel substances, they also form part of the subject-matter of the present application.

The novel azinethiones of the general formula (V) are obtained when azinones of the general formula (IX)

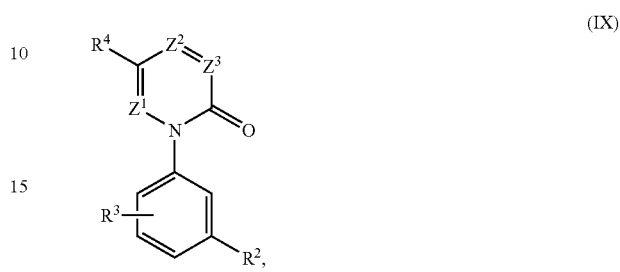

(IX)

in which
$R^2$, $R^3$, $R^4$, $Z^1$, $Z^2$ and $Z^3$ are each as defined above
are reacted with a sulphurizing agent, such as, for example, phosphorus(V) sulphide ($P_2S_5$ or $P_4S_{10}$), if appropriate in the presence of a reaction auxiliary, such as, for example, pyridine, at temperatures between 10° C. and 150° C. (cf. Preparation Examples).

The starting materials of the general formula (IX) are known and/or can be prepared by processes known per se (cf. Chem. Pharm. Bull. 45 (1997), 719–721, DE-A-1 900 947, DE-A-2 362 958, DE-A-2 555 411, cf. also the Preparation Examples).

The azinones of the general formula (IX) are obtained when azinones of the general formula (X)

(X)

in which
$R^4$, $Z^1$, $Z^2$ and $Z^3$ are each as defined above
are reacted with halogenoarenes of the general formula (XI)

(XI)

in which
$R^2$ and $R^3$ are each as defined above and
$X^2$ represents fluorine, chlorine, bromine or iodine,
if appropriate in the presence of a catalyst, such as, for example, copper(I) iodide, if appropriate in the presence of an acid acceptor, such as, for example, potassium carbonate, and if appropriate in the presence of a diluent, such as, for example, N,N-dimethyl-formamide, at temperatures between 20° C. and 200° C. (cf. the Preparation Examples).

The formula (VII) provides a general definition of the chloroazinium compounds to be used as starting materials in the process (c) according to the invention for preparing compounds of the general formula (I). In the general formula (VII), $R^2$, $R^3$, $R^4$, $Z^1$, $Z^2$ and $Z^3$ each preferably have those meanings which have already been mentioned above, in connection with the description of the compounds of the general formula (I) according to the invention, as being preferred, particularly preferred or very particularly preferred for $R^2$, $R^3$, $R^4$, $Z^1$, $Z^2$ and $Z^3$.

The starting materials of the general formula (VII) have hitherto not being disclosed in the literature; as novel substances, they also form part of the subject-matter of the present application.

The novel chloroazinium compounds of the general formula (VII) are obtained when azinones of the general formula (IX)

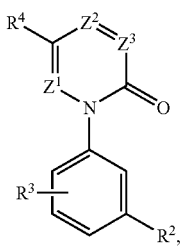

in which
$R^2$, $R^3$, $R^4$, $Z^1$, $Z^2$ and $Z^3$ are each as defined above
are reacted with chlorinating agents, such as, for example,
phosgene, diphosgene, oxalyl chloride, thionyl chloride, phosphorus(III) chloride, phosphoryl chloride or phosphorus(V) chloride, if appropriate in the presence of reaction auxiliaries, such as, for example, N,N-dimethylformamide, and if appropriate in the presence of diluents, such as, for example, 1,2-dichloro-ethane, at temperatures between 0° C. and 150° C. (cf. the Preparation Examples).

The formula (VIII) provides a general definition of the amino compounds further to be used as starting materials in the process (c) according to the invention for preparing compounds of the general formula (I). In the general formula (VIII), $R^1$ preferably has that meaning which has already been mentioned above, in connection with the description of the compounds of the general formula (I) according to the invention, as being preferred, particularly preferred or very particularly preferred for $R^1$.

The starting materials of the general formula (VIII) are known chemicals for synthesis.

Suitable reaction auxiliaries for the processes (a) and (c) according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

Further reaction auxiliaries suitable for the processes (a) and (c) according to the invention are phase-transfer catalysts. Examples of such catalysts which may be mentioned are:

tetrabutylammonium bromide, tetrabutylammonium chloride, tetraoctylammonium chloride, tetrabutylammonium hydrogen sulphate, methyl-trioctylammonium chloride, hexadecyl-trimethylammonium chloride, hexadecyl-trimethylammonium bromide, benzyl-trimethylammonium chloride, benzyl-triethylammonium chloride, benzyl-trimethylammonium hydroxide, benzyl-triethylammonium hydroxide, benzyl-tributylammonium chloride, benzyl-tributylammonium bromide, tetrabutylphosphonium bromide, tetrabutylphosphonium chloride, tributyl-hexadecylphosphonium bromide, butyl-triphenylphosphonium chloride, ethyl-trioctylphosphonium bromide, tetraphenylphosphonium bromide.

Suitable reaction auxiliaries and/or diluents for the process (d) according to the invention are substances which are generally used for nitrations. These preferably include sulphuric acid, acetic acid and acetic anhydride.

The processes (a), (b) and (c) for preparing the compounds of the general formula (I) are preferably carried out using one or more diluents. Suitable diluents for carrying out the processes (a), (b) and (c) according to the invention are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitriles, amides, such as N,N-dimethylformamide, N,N-dimethylacetamide, N-methyl-formanilide, N-methylpyrrolidone or hexamethylphosphoric triamide; esters, such as methyl acetate or ethyl acetate; sulphoxides, such as dimethyl sulphoxide; alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the processes (a), (b), (c) and (d) according to the invention, the reaction temperatures can be varied within a relatively wide range. In general, the processes are carried out at temperatures between −30 C. and −150° C., preferably between −10° C. and 120° C.

The processes according to the invention are generally carried out under atmospheric pressure. However, it is also possible to carry out the processes according to the invention under elevated or reduced pressure—in general between 0.1 bar and 10 bar.

For carrying out the processes according to the invention, the starting materials are generally employed in approximately equimolar amounts. However, it is also possible to use a relatively large excess of one of the components. The reaction is generally carried out in a suitable diluent, in the presence of an appropriate reaction auxiliary, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) and the compounds of the formulae (IX) and (IXa) according to the invention have strong herbicidal activity and a broad activity spectrum when used on the soil or on above-ground parts of plants. To a certain extent, they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as saw-dust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or lattices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible Components for the Mixtures are Known Herbicides, for Example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazone, benzfendizone, benzobicyclon, benzofenap, benzoylprop(-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl (-ethyl), difenzoquat, diflufenican, diflufenzopyr, dimefuron, dimepiperate, dimethachlor, dimethametryn, dimethenarnid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxy-sulfuron, etobenzanid, fenoxaprop (—P-ethyl), fentrazamide, flamprop (-isopropyl, -isopropyl-L, -methyl), flazasulfuron, florasulam, fluazifop (—P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop(-ethoxyethyl, —P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (—P-ethyl, —P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention is illustrated by the examples below.

PREPARATION EXAMPLES

Example 1

(Process (a))

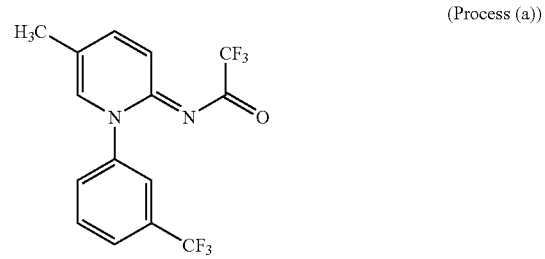

A mixture of 2.3 g (10 mmol) of 5-methyl-1-(3-trifluoromethyl-phenyl)-2(1H)-pyridineimine, 2.1 g (10 mmol) of trifluoroacetic anhydride, 1.0 g (10 mmol) of triethylamine and 50 ml of ethyl acetate is stirred at room temperature (about 20° C.) for 60 minutes. The reaction mixture is then washed with water, dried with sodium sulphate and filtered. The filtrate is concentrated under water pump vacuum, the residue is digested with diisopropyl ether and the resulting crystalline product is isolated by filtration with suction.

This gives 0.5 g (14% of theory) of 2,2,2-trifluoro-N-[5-methyl-1-(3-trifluoromethyl-phenyl)-2(1H)-pyridinylidene]-acetamide of melting point 115° C.

Example 2

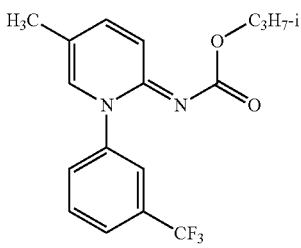
(Process (a))

A mixture of 1.1 g (4 mmol) of 5-methyl-1-(3-trifluoromethyl-phenyl)-2(1H)-pyridineimine, 5 ml (5 mmol) of isopropyl chloroformate, 0.5 g (5 mmol) of triethylamine and 50 ml of ethyl acetate is stirred at room temperature (about 20° C.) for 60 minutes. The reaction mixture is then washed with water, the aqueous phase is reextracted with methylene chloride and the combined organic phases are dried with sodium sulphate and filtered. From the filtrate, the solvents are carefully distilled off under reduced pressure.

This gives 0.6 g (46% of theory) of O-methyl N-[5-methyl-1-(3-trifluoromethyl-phenyl)-2(1H)-pyridinylidene]-carbamate as an amorphous residue.

log P=1.59 (determination of log P values see page 40).

Example 3

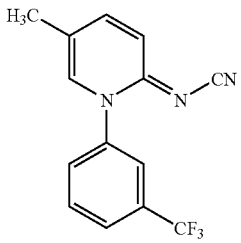
(Process (a))

A mixture of 1.1 g (4 mmol) of 5-methyl-1-(3-trifluoromethyl-phenyl)-2(1H)-pyridineimine, 0.6 g (5 mmol) of cyanogen bromide, 0.5 g (5 mmol) of triethylamine and 50 ml of ethyl acetate and stirred at room temperature (about. 20° C.) for 30 minutes. The reaction mixture is then washed with water, the aqueous phase is reextracted with methylene chloride and the combined organic phases are dried with sodium sulphate and filtered. From the filtrate, the solvents are carefully distilled off under reduced pressure.

This gives 0.35 g (32% of theory) of 5-methyl-1-(3-trifluoromethyl-phenyl)-2(1H)-pyridinylidenecyanamide of melting point 165° C.

Example 4

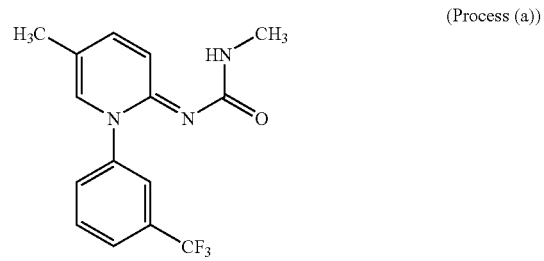
(Process (a))

A mixture of 2.6 g (10 mmol) of 5-methyl-1-(3-trifluoromethyl-phenyl)-2(1H)-pyridineimine, 0.6 g (10 mmol) of methyl isocyanate and 100 ml of acetonitrile is allowed to stand at room temperature (about 20° C.) for two hours. The mixture is then concentrated under water pump vacuum, the residue is digested with diisopropyl ether and the resulting crystalline product is isolated by filtration with suction.

This gives 2.1 g (68% of theory) of N-methyl-N'-[5-methyl-1-(3-trifluoromethyl-phenyl)-2(1H)-pyridinylidene]-urea of melting point 114° C.

Example 5

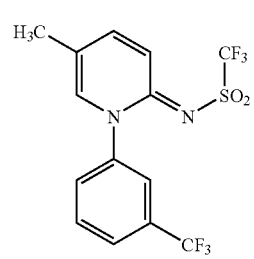
(Process (a))

2.9 g (10 mmol) of 5-methyl-1-(3-trifluoromethyl-phenyl)-2(1H)-pyridinimine hydrochloride, 3.1 g (30 mmol) of triethylamine and 100 ml of acetonitrile is, at room temperature (about 20° C.) and with stirring, admixed dropwise with 2.9 g (10 mmol) of trifluoromethanesulphonic anhydride. The reaction mixture is stirred at room temperature for 60 minutes and then concentrated under water pump vacuum. The crude product obtained as residue is purified by column chromatography (silica gel, ethyl acetate/hexane, 9:1).

This gives 0.40 g (10% of theory) of N-[5-methyl-1-(3-trifluoromethyl-phenyl)-2(1H)-pyridinylidene]-trifluoromethanesulphonamide of melting point 206° C.

Example 6

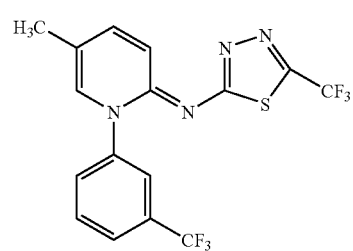
(Process (a))

A mixture of 2.9 g (10 mmol) of 5-methyl-1-(3-trifluoromethyl-phenyl)-2(1H)-pyridinimine hydrochloride, 2.3 g (10 mmol) of 2-methylsulphonyl-5-trifluoromethyl-1,3,4-thiadiazole, 4.2 g (30 mmol) of calcium carbonate and 30 ml of dimethyl sulphoxide is stirred at 100° C. for 60 minutes and, after cooling, poured into about the same volume of methylene chloride. The organic phase is washed with water and saturated aqueous sodium chloride solution and then dried with sodium sulphate and filtered. The filtrate is concentrated under water pump vacuum, the residue is digested with diethyl ether and the resulting crystalline product is isolated by filtration with suction.

This gives 2.3 g (57% of theory) of N-(5-trifluoromethyl-1,3,4-thiadiazol-2-yl)-5-methyl-1-(3-trifluoromethyl-phenyl)-2(1H)-pyridinimine of melting point 179° C.

Example 7

(Process (b))

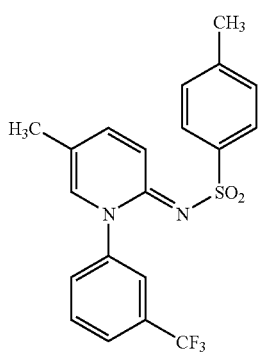

2.7 g (10 mmol) of 5-methyl-1-(3-trifluoromethyl-phenyl)-2(1H)-pyridinethione are initially charged in 50 ml of chloroform and, at room temperature (about 20° C.) and with stirring, admixed dropwise with a solution of 2.9 g (10 mmol) of N-chloro-p-toluenesulphonamide sodium salt hydrate (chloramine T hydrate) in 50 ml of ethanol. The reaction mixture is stirred at room temperature for 15 hours and then concentrated under water pump vacuum, and the residue is taken up in chloroform, washed with water and then with saturated aqueous sodium bicarbonate solution, dried with sodium sulphate and filtered. The filtrate is concentrated under water pump vacuum and the residue is kept under high vacuum at 180° C. for 15 minutes. After cooling and digestion with diisopropyl ether, the resulting crystalline product is isolated by filtration with suction.

This gives 1.8 g (49% of theory) of 4-methyl-N-[5-methyl-1-(3-trifluoromethyl-phenyl)-2(1H)-pyridinylidene]-benzenesulphonamide of melting point 174° C.

Example 8

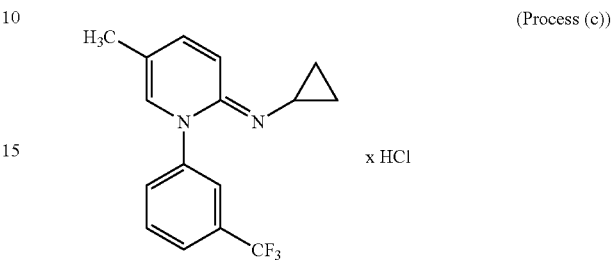

A mixture of 1.6 g (5 mmol) of 2-chloro-5-methyl-1-(3-trifluoromethyl-phenyl)-pyridinium chloride, 0.9 g (15 mmol) of cyclopropylamine and 50 ml of methanol is allowed to stand at room temperature (about 20° C.) for 15 hours and then concentrated under water pump vacuum. The residue is taken up in methylene chloride, washed with water, dried with sodium sulphate and filtered. The filtrate is concentrated under water pump vacuum, the residue is taken up in methanol and hydrochloric acid and the volatile components are carefully distilled off under reduced pressure. The crude product obtained as residue is purified by column chromatography (silica gel, ethyl acetate/hexane, 5:1).

This gives 1.5 g (91% of theory) of N-cyclopropyl-5-methyl-1-(3-trifluoromethyl-phenyl)-2(1H)-pyridineimine as an oily product.

log P=1.51 (determination of log P values see page 40).

Analogously to Examples 1 to 8, and in accordance with the general description of the preparation process according to the invention, it is also possible to prepare, for example, the compounds of the general formula (I) listed in Table 1 below.

TABLE

Examples of compounds of the formula (I)

| Ex. No. | $R^1$ | $R^2$ | (Position) $R^3$ | $R^4$ | $Z^1$ | $Z^2$ | $Z^3$ | Physical data |
|---|---|---|---|---|---|---|---|---|
| 9 | 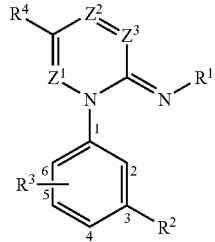 | $CF_3$ | — | $CH_3$ | CH | CH | CH | m.p.: 121° C. |

TABLE-continued

Examples of compounds of the formula (I)

| Ex. No. | R¹ | R² | (Position) R³ | R⁴ | Z¹ | Z² | Z³ | Physical data |
|---|---|---|---|---|---|---|---|---|
| 10 | C(O)-C₆H₅ (acetophenone group) | CF₃ | — | CH₃ | CH | CH | CH | m.p.: 175° C. |
| 11 | S-C₂H₅ thioester (C(O)SC₂H₅) | CF₃ | — | CH₃ | CH | CH | CH | m.p.: 124° C. |
| 12 | NH-C(CH₃)₃ (C(O)NHC(CH₃)₃) | CF₃ | — | CH₃ | CH | CH | CH | m.p.: 156° C. |
| 13 | NH-C₃H₇-i (C(S)NHC₃H₇-i) | CF₃ | — | CH₃ | CH | CH | CH | m.p.: 139° C. |
| 14 | S-C₃H₇-i (C(O)SC₃H₇-i) | CF₃ | — | CH₃ | CH | CH | CH | m.p.: 140° C. |
| 15 | —CO—CF₃ | CF₃ | — | CH₃ | N | CH | CH | m.p.: 128° C. |
| 16 | —CH₂—C₆H₅ | CF₃ | — | CH₃ | CH | CH | CH | m.p.: 253° C. |
| 17 | —CO—C₃H₇-i | CF₃ | — | CH₃ | CH | CH | CH | m.p.: 93° C. |
| 18 | C(O)-cyclopropyl | CF₃ | — | CH₃ | CH | CH | CH | m.p.: 98° C. |
| 19 | —CO—CHF₂ | CF₃ | — | CH₃ | CH | CH | CH | m.p.: 137° C. |
| 20 | 2-methyl-4,6-dimethoxypyrimidin-yl | CF₃ | — | CH₃ | CH | CH | CH | m.p.: 165° C. |
| 21 | 2-(trifluoromethyl)phenyl-SO₂— | CF₃ | — | CH₃ | CH | CH | CH | m.p.: 148° C. |

TABLE-continued

Examples of compounds of the formula (I)

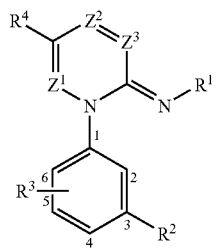

| Ex. No. | R¹ | R² | (Position) R³ | R⁴ | Z¹ | Z² | Z³ | Physical data |
|---|---|---|---|---|---|---|---|---|
| 22 | CH₂=CH-CH₂-O-CH₂- | CF₃ | — | CH₃ | CH | CH | CH | logP = 1,58 a) |
| 23 | (O=C(NH-)C₃H₇-i)-CH₂- | CF₃ | — | CH₃ | CH | CH | CH | m.p.: 188° C. |
| 24 | —CO—CF₃ | CF₃ | — | H | CH | CH | CH | m.p.: 150° C. |
| 25 | —CO—CF₃ | CF₃ | (4) F | CH₃ | CH | CH | CH | m.p.: 180° C. |
| 26 | —CO—CF₃ | CF₃ | (5) F | CH₃ | CH | CH | CH | m.p.: 158° C. |
| 27 | 1-CH₃-3-CH₃-5-F-pyrazol-4-yl-CO— | CF₃ | — | CH₃ | CH | CH | CH | m.p.: 179° C. |
| 28 | 2-CH₃-4-CF₃-thiazol-5-yl-CO— | CF₃ | — | CH₃ | CH | CH | CH | m.p.: 201° C. |
| 29 | —CN | CF₃ | — | CH₃ | N | CH | CH | m.p.: 148° C. |
| 30 | —CO—CH₃ | CF₃ | — | CH₃ | CH | CH | CH | m.p.: 101° C. |
| 31 | —CO—C₂H₅ | CF₃ | — | CH₃ | CH | CH | CH | m.p.: 113° C. |
| 32 | —CO—C₃H₇-n | CF₃ | — | CH₃ | CH | CH | CH | m.p.: 103° C. |
| 33 | CH₃—O—CO—CH₂— | CF₃ | — | CH₃ | CH | CH | CH | m.p.: 133° C. |
| 34 | C₂H₅—O—CO—CH₂— | CF₃ | — | CH₃ | CH | CH | CH | m.p.: 150° C. |
| 35 | C₃H₇-n—O—CO—CH₂— | CF₃ | — | CH₃ | CH | CH | CH | m.p.: 85° C. |

TABLE-continued

Examples of compounds of the formula (I)

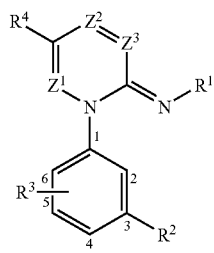

| Ex. No. | R¹ | R² | (Position) R³ | R⁴ | Z¹ | Z² | Z³ | Physical data |
|---|---|---|---|---|---|---|---|---|
| 36 | S-CH₃ acetyl | CF₃ | — | CH₃ | CH | CH | CH | m.p.: 103° C. |
| 37 | 2,4-dichlorophenyl ketone | CF₃ | — | CH₃ | CH | CH | CH | m.p.: 181° C. |
| 38 | —CO—C₄H₉-t | CF₃ | — | CH₃ | CH | CH | CH | m.p.: 77° C. |
| 39 | O-C₄H₉-t acetyl | CF₃ | — | CH₃ | CH | CH | CH | m.p.: 108° C. |
| 40 | O-CH₃ acetyl | CF₃ | — | CH₃ | N | CH | CH | m.p.: 148° C. |
| 41 | O-C₂H₅ acetyl | CF₃ | — | CH₃ | N | CH | CH | m.p.: 146° C. |
| 42 | O-C₃H₇-n acetyl | CF₃ | — | CH₃ | N | CH | CH | m.p.: 98° C. |
| 43 | O-C₃H₇-i acetyl | CF₃ | — | CH₃ | N | CH | CH | m.p.: 123° C. |
| 44 | O-C₃H₇-i acetyl | CF₃ | — | CH₃ | N | CH | CH | m.p.: 83° C. |

TABLE-continued

Examples of compounds of the formula (I)

| Ex. No. | R¹ | R² | (Position) R³ | R⁴ | Z¹ | Z² | Z³ | Physical data |
|---|---|---|---|---|---|---|---|---|
| 45 | (1-cyclopropyl-1-oxo-propan-2-yl) | CF₃ | — | CH₃ | N | CH | CH | m.p.: 108° C. |
| 46 | (1-(2,4-dichlorophenyl)-1-oxo-propan-2-yl) | CF₃ | — | CH₃ | N | CH | CH | m.p.: 164° C. |
| 47 | (3-fluoro-4-(difluoromethylene)-1-oxo-pentan-2-yl) | CF₃ | — | CH₃ | N | CH | CH | m.p.: 85° C. |
| 48 | (N-(2,4-difluorophenyl)acetamido) | CF₃ | — | CH₃ | N | CH | CH | m.p.: 157° C. |

Log P values given in Table 1 were determined in accordance with EEC Directive 79/831 Annex V.A8 by HPLC (High Performance Liquid Chromatography) on a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding data in Table 1 are labelled $^{a)}$.

(b) Mobile phases for the determination in the neutral range: 0.01 molar aqueous phosphate buffer solution, acetonitrile; linear gradient from 10% acetonitrile to 90% acetonitrile—the corresponding data in Table 1 are labelled $^{b)}$.

The calibration was carried out using unbranched alkan-2-ones (having 3 to 16 carbon atoms) with known log P values (determination of the log P values by the retention times using linear interpolation between two successive alkanones).

The lambda max values were determined in the maxima of the chromatographic signals using the UV spectra from 200 nm to 400 nm.

Starting Materials of the Formula (II):

Example (II-1)

(Process (α))

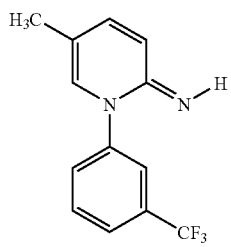

-continued

Step 1

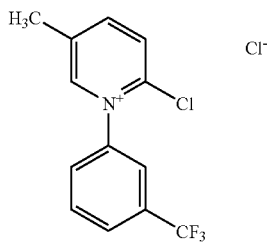

A mixture of 2.5 g (10 mmol) of 5-methyl-1-(3-trifluoromethyl-phenyl)-2(1H)-pyridone, 3.9 g (30 mmol) of oxalyl chloride, 40 ml of 1,2-dichloro-ethane and 2 drops of N,N-dimethyl-formamide is heated at the boil under reflux until the evolution of gas has ceased. After cooling to room temperature, the resulting crystalline product is isolated by filtration with suction.

This gives 2.1 g (65% of theory) of 2-chloro-5-methyl-1 (3-trifluoromethyl-phenyl)-pyridinium chloride of melting point 194° C.

Step 2

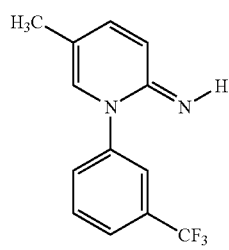

3.1 g (10 mmol) of 2-chloro-5-methyl-1-(3-trifluoromethyl-phenyl)-pyridinium chloride are taken up in 40 ml of methanol and, at temperatures between 20° C. and 30° C., ammonia is introduced into this mixture until the solution is saturated. 3.6 g of (20 mmol) of sodium methoxide are then added in the form of a 30% strength solution in methanol, and the mixture is then concentrated under water pump vacuum.

The resulting product (5-methyl-1-(3-trifluoromethyl-phenyl)-2(1H)-pyridineimine) can be reacted according to the process (a) according to the invention without any further purification.

Example (II-1)

(Process (β))

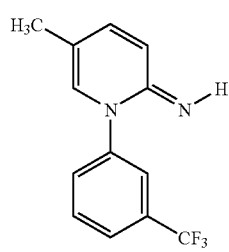

A mixture of 10 g (24 mmol) of 4-methyl-N-[5-methyl-1-(3-trifluoromethyl-phenyl)-2(1H)-pyridinylidene]-benzenesulphonamide and 50 g of 80% strength sulphuric acid is stirred at 50° C. for 15 hours and then added dropwise to a 1 molar aqueous sodium carbonate solution. The mixture is then extracted with ethyl acetate and the organic phase is dried with sodium sulphate and filtered. From the filtrate, the solvent is carefully distilled off under reduced pressure.

This gives 2.3 g (38% of theory) of 5-methyl-1-(3-trifluoromethyl-phenyl)-2(1H)-pyridineimine which can be reacted according to the process (a) according to the invention without any further purification.

Analogously to Example (II-1), it is also possible to prepare, for example, the compounds of the general formula (II) listed in Table 2 below.

TABLE 2

Examples of the compounds of the formula (II) the compounds in each case being the hydrochlorides

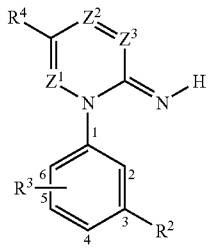

(II)

| Ex. No. | $R^2$ | (Position) $R^3$ | $R^4$ | $Z^1$ | $Z^2$ | $Z^3$ | Physical data |
|---|---|---|---|---|---|---|---|
| II-2 | $CF_3$ | — | H | CH | CH | CH | m.p.: 269° C. |
| II-3 | CN | — | $CH_3$ | CH | CH | CH | |
| II-4 | Cl | — | $CH_3$ | CH | CH | CH | |
| II-5 | $CF_3$ | — | Cl | CH | CH | CH | |
| II-6 | Br | — | $CH_3$ | CH | CH | CH | |
| II-7 | $CF_3$ | — | CN | CH | CH | CH | |
| II-8 | $OCF_3$ | — | $CH_3$ | CH | CH | CH | |
| II-9 | $CF_3$ | — | $C_2H_5$ | CH | CH | CH | |
| II-10 | $CF_3$ | — | $C_3H_7$-n | CH | CH | CH | |
| II-11 | $CF_3$ | — | $C_3H_7$-i | CH | CH | CH | |
| II-12 | $OCHF_2$ | — | $CH_3$ | CH | CH | CH | |
| II-13 | $CF_3$ | (2) F | $CH_3$ | CH | CH | CH | |
| II-14 | $CF_3$ | (4) F | $CH_3$ | CH | CH | CH | m.p.: 250° C. |
| II-15 | $CF_3$ | (5) F | $CH_3$ | CH | CH | CH | m.p.: 250° C. |
| II-16 | $CF_3$ | (6) F | $CH_3$ | CH | CH | CH | |
| II-17 | $NO_2$ | — | $CH_3$ | CH | CH | CH | |
| II-18 | $SO_2CH_3$ | — | $CH_3$ | CH | CH | CH | |
| II-19 | $SO_2C_2H_5$ | — | $CH_3$ | CH | CH | CH | |
| II-20 | $CF_3$ | — | $CH_3$ | CH | N | CH | |
| II-21 | $CF_3$ | — | $CH_3$ | CH | CH | N | |
| II-22 | $CF_3$ | — | $CH_3$ | N | N | CH | |
| II-23 | $CF_3$ | — | $CH_3$ | N | CH | N | |
| II-24 | $CF_3$ | — | $CH_3$ | CH | N | N | |
| II-25 | $CF_3$ | — | $CH_3$ | N | CH | CH | $^1$H-NMR (DMSO-$D_6^\delta$): 2.43 ppm. |

Example (II-26)

5-methyl-1-(2,3-difluoromethylenedioxy-phenyl)-2 (1H)-pyridineimine

Example (II-27)

5-methyl-1-(3,4-difluoromethylenedioxy-phenyl)-2 (1H)-pyridineimine

Example (II-28)

5-methyl-1-(2,3-tetrafluoroethylenedioxy-phenyl)-2 (1H)-pyridineimine

Example (II-29)

5-methyl-1-(3,4-tetrafluoroethylenedioxy-phenyl)-2(1H)-pyridineimine

Example (II-30)

5-methyl-1-(2,3-chlorotrifluoroethylenedioxy-phenyl)-2(1H)-pyridineimine

Example (II-31)

5-methyl-1-(3,4-chlorotrifluoroethylenedioxy-phenyl)-2(1H)-pyridineimine

Starting Materials of the Formula (V):

Example (V-1)

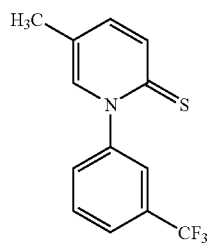

A mixture of 18.7 g (74 mmol) of 5-methyl-1-(3-trifluoromethyl-phenyl)-2(1H)-pyridinone, 16.4 g (74 mmol) of phosphorus(V) sulphide and 75 ml of pyridine is heated under reflux for two hours and, after cooling, poured into 300 ml of water. The mixture is stirred overnight and the resulting crystalline product is then isolated by filtration with suction.

This gives 12.8 g (64% of theory) of 5-methyl-1-(3-trifluoromethyl-phenyl)-2(1H)-pyridinethione of melting point 96° C.

Analogously to Example (V-1), it is also possible to prepare, for example, the compounds of the general formula (V) listed in Table 3 below.

TABLE 3

Examples of the compounds of the formula (V)

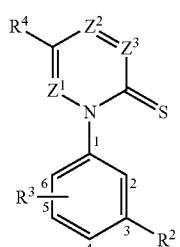

| Ex. No. | $R^2$ | (Position) $R^3$ | $R^4$ | $Z^1$ | $Z^2$ | $Z^3$ |
|---|---|---|---|---|---|---|
| V-2 | $CF_3$ | — | H | CH | CH | CH |
| V-3 | CN | — | $CH_3$ | CH | CH | CH |
| V-4 | Cl | — | $CH_3$ | CH | CH | CH |
| V-5 | $CF_3$ | — | Cl | CH | CH | CH |
| V-6 | Br | — | $CH_3$ | CH | CH | CH |
| V-7 | $CF_3$ | — | CN | CH | CH | CH |
| V-8 | $CF_3$ | — | $C_2H_5$ | CH | CH | CH |
| V-9 | $OCF_3$ | — | $CH_3$ | CH | CH | CH |
| V-10 | $OCF_3$ | — | $C_2H_5$ | CH | CH | CH |
| V-11 | $CF_3$ | — | $C_3H_7$-i | CH | CH | CH |
| V-12 | $OCHF_2$ | — | $CH_3$ | CH | CH | CH |
| V-13 | $CF_3$ | (2) F | $CH_3$ | CH | CH | CH |
| V-14 | $CF_3$ | (4) F | $CH_3$ | CH | CH | CH |
| V-15 | $CF_3$ | (5) F | $CH_3$ | CH | CH | CH |
| V-16 | $CF_3$ | (6) F | $CH_3$ | CH | CH | CH |
| V-17 | $NO_2$ | — | $CH_3$ | CH | CH | CH |
| V-18 | $SO_2CH_3$ | — | $CH_3$ | CH | CH | CH |
| V-19 | $SO_2C_2H_5$ | — | $CH_3$ | CH | CH | CH |
| V-20 | $CF_3$ | — | $CH_3$ | CH | N | CH |
| V-21 | $CF_3$ | — | $CH_3$ | CH | CH | N |
| V-22 | $CF_3$ | — | $CH_3$ | N | N | CH |
| V-23 | $CF_3$ | — | $CH_3$ | N | CH | N |
| V-24 | $CF_3$ | — | $CH_3$ | CH | N | N |
| V-25 | $CF_3$ | — | $CH_3$ | N | CH | CH |

Example (V-26)

5-methyl-1-(2,3-difluoromethylenedioxy-phenyl)-2(1H)-pyridinethione

Example (V-27)

5-methyl-1-(3,4-difluoromethylenedioxy-phenyl)-2(1H)-pyridinethione

Example (V-28)

5-methyl-1-(2,3-tetrafluoroethylenedioxy-phenyl)-2(1H)-pyridinethione

Example (V-29)

5-methyl-1-(3,4-tetrafluoroethylenedioxy-phenyl)-2(1H)-pyridinethione

Example (V-30)

5-methyl-1-(2,3-chlorotrifluoroethylenedioxy-phenyl)-2(1H)-pyridinethione

Example (V-31)

5-methyl-1-(3,4-chlorotrifluoroethylenedioxy-phenyl)-2(1H)-pyridinethione

Intermediates of the Formula (VII):

Example (VII-1)

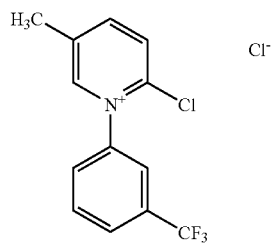

A mixture of 2.5 g (10 mmol) of 5-methyl-1-(3-trifluoromethyl-phenyl)-2(1H)-pyridone, 3.9 g (30 mmol) of oxalyl chloride, 40 ml of 1,2-dichloro-ethane and 2 drops of N,N-dimethyl-formamide is stirred at the boil under reflux until the evolution of gas has ceased. After cooling to room temperature, the resulting crystalline product is isolated by filtration with suction.

This gives 2.1 g (65% of theory) of 2-chloro-5-methyl-1-(3-trifluoromethyl-phenyl)-pyridinium chloride of melting point 194° C.

Analogously to Example (VII-1), it is also possible to prepare, for example, the compounds of the general formula (VII) listed in Table 4 below.

Example (VII-26)

2-chloro-5-methyl-1-(2,3-difluoromethylenedioxy-phenyl)-pyridinium chloride

Example (VII-27)

2-chloro-5-methyl-1-(3,4-difluoromethylenedioxy-phenyl)-pyridinium chloride

Example (VII-28)

2-chloro-5-methyl-1-(2,3-tetrafluoroethylenedioxy-phenyl)-pyridinium chloride

Example (VII-29)

2-chloro-5-methyl-1-(3,4-tetrafluoroethylenedioxy-phenyl)-pyridinium chloride

Example (VII-30)

2-chloro-5-methyl-1-(2,3-chlorotrifluoroethylene-dioxy-phenyl)-pyridinium chloride

TABLE 4

Examples of compounds of the formula (VII)

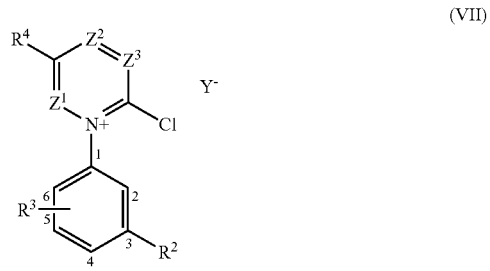

(VII)

| Ex. No. | $R^2$ | (Position) $R^3$ | $R^4$ | $Z^1$ | $Z^2$ | $Z^3$ | Physical data |
|---|---|---|---|---|---|---|---|
| VII-2 | $CF_3$ | — | H | CH | CH | CH | m.p.: 74° C. |
| VII-3 | CN | — | $CH_3$ | CH | CH | CH | |
| VII-4 | Cl | — | $CH_3$ | CH | CH | CH | |
| VII-5 | $CF_3$ | — | Cl | CH | CH | CH | |
| VII-6 | Br | — | $CH_3$ | CH | CH | CH | |
| VII-7 | $CF_3$ | — | CN | CH | CH | CH | |
| VII-8 | $CF_3$ | — | $C_2H_5$ | CH | CH | CH | |
| VII-9 | $OCF_3$ | — | $CH_3$ | CH | CH | CH | |
| VII-10 | $OCF_3$ | — | $C_2H_5$ | CH | CH | CH | |
| VII-11 | $CF_3$ | — | $C_3H_7$-i | CH | CH | CH | |
| VII-12 | $OCHF_2$ | — | $CH_3$ | CH | CH | CH | |
| VII-13 | $CF_3$ | (2) F | $CH_3$ | CH | CH | CH | |
| VII-14 | $CF_3$ | (4) F | $CH_3$ | CH | CH | CH | m.p.: 250° C. |
| VII-15 | $CF_3$ | (5) F | $CH_3$ | CH | CH | CH | m.p.: 265° C. |
| VII-16 | $CF_3$ | (6) F | $CH_3$ | CH | CH | CH | |
| VII-17 | $NO_2$ | — | $CH_3$ | CH | CH | CH | |
| VII-18 | $SO_2CH_3$ | — | $CH_3$ | CH | CH | CH | |
| VII-19 | $CF_3$ | — | $CH_3$ | CH | N | CH | |
| VII-20 | $CF_3$ | — | $CH_3$ | CH | CH | N | |
| VII-21 | $CF_3$ | — | $CH_3$ | N | N | CH | |
| VII-22 | $CF_3$ | — | $CH_3$ | N | CH | N | |
| VII-23 | $CF_3$ | — | $CH_3$ | CH | N | N | |
| VII-24 | $CF_3$ | — | $CH_3$ | N | CH | CH | logP 2.23 [a)] |
| VII-25 | $CF_3$ | — | H | CH | CH | C—$CH_3$ | m.p.: 218° C. |

Y in each case represents Cl

Example (VII-31)

2-chloro-5-methyl-1-(3,4-chlorotrifluoroethylene-dioxy-phenyl)-pyridinium chloride Starting Materials of the Formula (IX):

Example (IX-1)

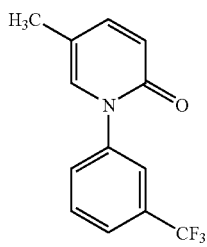

A mixture of 21.8 g (0.20 mol) of 5-methyl-2-pyridone, 54 g (0.24 mol) of 3-bromo-benzotrifluoride, 27.7 g (0.20 mol) of potassium carbonate, 2 g (10 mmol) of copper (I) iodide and 300 ml of N,N-dimethyl-formamide is stirred at 100° C. for 15 hours and at 140° C. for a further 6 hours. After cooling to room temperature, the mixture is admixed with 300 ml of ethyl acetate and then diluted with water to about twice its original volume. The organic phase is separated off and the aqueous phase is reextracted with ethyl acetate. The combined organic phases are washed with water, dried with sodium sulphate and filtered. From the filtrate, the solvent is fully distilled off under reduced pressure.

This gives 20.7 g (41% of theory) of 5-methyl-1-(3-trifluoromethyl-phenyl)-2(1H)-pyridinone of melting point 95° C.

Analogously to Example (IX-1), it is also possible to prepare, for example, the compounds of the general formula (IX) listed in Table 5 below.

TABLE 5

Examples of compounds of the formula (IX)

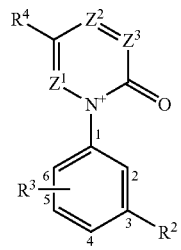

(IX)

| Ex. No. | $R^2$ | (Position) $R^3$ | $R^4$ | $Z^1$ | $Z^2$ | $Z^3$ | Physical data |
|---|---|---|---|---|---|---|---|
| IX-2 | $CF_3$ | — | H | CH | CH | CH | m.p.: 63° C. |
| IX-3 | CN | — | $CH_3$ | CH | CH | CH | m.p.: 188° C. |
| IX-4 | Cl | — | $CH_3$ | CH | CH | CH | |
| IX-5 | $CF_3$ | — | Cl | CH | CH | CH | |
| IX-6 | Br | — | $CH_3$ | CH | CH | CH | |
| IX-7 | $CF_3$ | — | CN | CH | CH | CH | |
| IX-8 | $CF_3$ | — | $C_2H_5$ | CH | CH | CH | |
| IX-9 | $CF_3$ | — | $CH_3$ | N | CH | CH | m.p.: 58° C. |
| IX-10 | $CF_3$ | (6) F | $CH_3$ | CH | CH | CH | |
| IX-11 | $OCF_3$ | — | $CH_3$ | CH | CH | CH | m.p.: 88° C. |
| IX-12 | $OCF_3$ | — | $C_2H_5$ | CH | CH | CH | |
| IX-13 | $CF_3$ | — | $C_3H_7$-i | CH | CH | CH | |
| IX-14 | $OCHF_2$ | — | $CH_3$ | CH | CH | CH | |
| IX-15 | $CF_3$ | (2) F | $CH_3$ | CH | CH | CH | |
| IX-16 | $CF_3$ | (4) F | $CH_3$ | CH | CH | CH | logP = 2,19 [a] |
| IX-17 | $CF_3$ | (5) F | $CH_3$ | CH | CH | CH | m.p.: 73° C. |
| IX-18 | $CF_3$ | (6) F | $C_2H_5$ | CH | CH | CH | |
| IX-19 | $NO_2$ | — | $CH_3$ | CH | CH | CH | |
| IX-20 | $SO_2CH_3$ | — | $CH_3$ | CH | CH | CH | |
| IX-21 | $CF_3$ | — | $CH_3$ | CH | N | CH | |
| IX-22 | $CF_3$ | — | $CH_3$ | CH | CH | N | |
| IX-23 | $CF_3$ | — | $CH_3$ | N | N | CH | |
| IX-24 | $CF_3$ | — | $CH_3$ | N | CH | N | |
| IX-25 | $CF_3$ | — | $CH_3$ | CH | N | N | |
| IX-26 | F | — | $CH_3$ | CH | CH | CH | m.p.: 132° C. |
| IX-27 | CF | — | $CH_3$ | CH | CH | C—$CH_3$ | log P = 2,56 [a] |

Example (IX-28)

5-methyl-1-(2,3-difluoromethylenedioxy-phenyl)-2(1H)-pyridinone (log P=3.95$^{a)}$)

Example (IX-29)

5-methyl-1-(3,4-difluoromethylenedioxy-phenyl)-2(1H)-pyridinone

Example (IX-30)

5-methyl-1-(2,3-tetrafluoroethylenedioxy-phenyl)-2(1H)-pyridinone

Example (IX-31)

5-methyl-1-(3,4-tetrafluoroethylenedioxy-phenyl)-2(1H)-pyridinone

Example (IX-32)

5-methyl-1-2,3-chlorotrifluoroethylenedioxy-phenyl)-2(1H)-pyridinone

Example (IX-33)

5-methyl-1-(3,4-chlorotrifluoroethylenedioxy-phenyl)-2(1H)-pyridinone

Example (IX-34)

3-methyl-1-(3-trifluoromethyl-phenyl)-2(1H)-pyridinone (m.p.: 122° C.),

Example (IX-35)

5-trifluoromethyl-1-(3-trifluoromethyl-phenyl)-2(1H)-pyridinone (log P=2.78$^{a)}$)

(Determination of Log P Values See Page 40)

USE EXAMPLES

Example A

Pre-emergence test

| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquors is chosen so that the particular amount of active compound desired is applied in 1000 liters of water per hectare.

After three weeks, the degree of damage to the plants is rated in % damage in comparison to the development of the untreated control. The figures denote:

0%=no effect (like untreated control)
100%=total destruction

In this test, for example, the compounds of Preparation Examples 1, 2, 3, IX-1, IX-3, IX-11 and IX16 exhibit strong activity against weeds, and some of them are tolerated well by crop plants, such as, for example, rice.

Example B

Post-Emergence Test

| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated controls.

The figures denote:

0%=no effect (like untreated control)
100%=total destruction

In this test, for example, the compounds of Preparation Examples 1, 3, IX-1 and IX-16 exhibit strong activity against weeds.

What is claimed is:

1. Substituted iminoazine of the general formula (I)

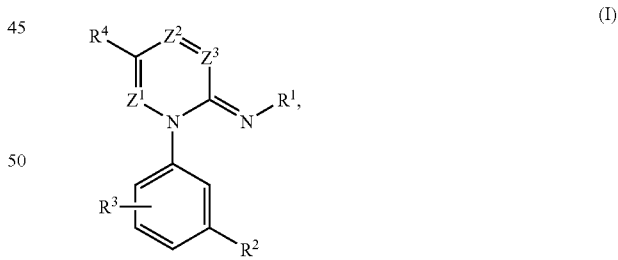

in which
$R^1$ represents nitro, cyano or one of the groups —$R^5$, —$CQ^1$-$Q^2$-$R^5$, —NH—$CQ^1$-$Q^2$-$R^5$ or —$SO_2$—$R^6$,
$R^2$ represents nitro, cyano, $SF_5$, halogen or in each case optionally substituted alkyl, alkoxy, alkylthio, alkylsulphinyl, alkylsulphonyl, or alkylsulphonyloxy,
$R^3$ represents hydrogen or halogen, or $R^3$ and $R^2$ together represent optionally substituted alkylenedioxy,
$R^4$ represents hydrogen, cyano, carboxyl, carbamoyl, halogen, or optionally substituted alkyl,
$Q^1$ represents O, S, or N—$R^5$,
$Q^2$ represents a single bond or represents O, S, or N—$R^5$, $R^5$ represents hydrogen, amino, or in each case optionally substituted alkyl, alkoxy, alkylamino, dialkylamino, alkylideneamino, alkenyl, alkenyloxy, alkynyl, cycloalkyl, cycloalkylamino, cycloalkylalkyl, aryl, arylamino, arylalkyl, heterocyclyl, or heterocyclylalkyl, $R^6$ represents in each case optionally substituted alkyl, alkenyl, cycloalkyl, cycloalkylalkyl, aryl, arylalkyl, heterocyclyl, or heterocyclylalkyl, $Z^1$ represents N or C—$R^4$, $Z^2$ represents N or C—$R^4$, and $Z^3$ represents N or C—$R^4$, with the proviso that $Z^2$ and $Z^3$ cannot both represent N.

2. A compound according to claim 1 in which $R^1$ represents cyano or one of the groups —$R^5$, —$CQ^1$-$Q^2$-$R^5$, —NH—$CQ^1$-$Q^2$-$R^5$, or —$SO_2$—$R^6$, $R^2$ represents nitro, cyano, $SF_5$, halogen, or in each case optionally cyano-, halogen-, or $C_1$–$C_4$-alkoxy-substituted alkyl, alkoxy, alkylthio, alkylsulphinyl, alkylsulphonyl, or alkylsulphonyloxy having in each case 1 to 5 carbon atoms, $R^3$ represents hydrogen or halogen, or $R^3$ and $R^2$ together represent optionally halogen-substituted alkylenedioxy having 1 to 3 carbon atoms, $R^4$ represents hydrogen, cyano, carboxyl, carbamoyl, halogen, or optionally cyano-, halogen-, or $C_1$–$C_4$-alkoxy-substituted alkyl having 1 to 5 carbon atoms, $Q^1$ represents O or S, $R^5$ represents hydrogen or amino, represents in each case optionally cyano-, halogen-, or $C_1$–$C_4$-alkoxy-substituted alkyl or alkoxy having in each case 1 to 6 carbon atoms, represents alkylamino having 1 to 6 carbon atoms, represents dialkylamino having in each case 1 to 6 carbon atoms in the alkyl groups, represents alkylideneamino having up to 6 carbon atoms, represents in each case optionally cyano- or halogen-substituted alkenyl, alkenyloxy, or alkynyl having in each case 2 to 6 carbon atoms, represents in each case optionally cyano-, halogen-, or $C_1$–$C_4$-alkyl-substituted cycloalkyl, represents cycloalkylamino or cycloalkylalkyl having in each case 3 to 6 carbon atoms in the cycloalkyl group and optionally 1 to 4 carbon atoms in the alkyl moiety, represents in each case optionally nitro-, cyano-, phenyl-, phenoxy-, phenylthio-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, or di-($C_1$–$C_4$-alkyl)-aminosulphonyl-substituted aryl, arylamino, or arylalkyl having in each case 6 or 10 carbon atoms in the aryl group and optionally 1 to 4 carbon atoms in the alkyl moiety, or represents in each case optionally nitro-, cyano-, phenyl-, phenoxy-, phenylthio-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, or di-($C_1$–$C_4$-alkyl)-aminosulphonyl-substituted monocyclic or bicyclic heterocyclyl or heterocyclylalkyl having in each case up to 10 carbon atoms and up to 4 nitrogen atoms and/or 1 or 2 oxygen or sulphur atoms in the heterocyclyl group and optionally 1 to 4 carbon atoms in the alkyl moiety, $R^6$ represents optionally halogen-substituted alkyl having 1 to 6 carbon atoms, represents optionally halogen-substituted alkenyl having 2 to 6 carbon atoms, represents optionally halogen- or $C_1$–$C_4$-alkyl-substituted cycloalkyl or cycloalkylalkyl having in each case 3 to 6 carbon atoms in the cycloalkyl group and optionally 1 to 4 carbon atoms in the alkyl moiety, represents in each case optionally nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, or di-($C_1$–$C_4$-alkyl)-aminosulphonyl-substituted aryl or arylalkyl having in each case 6 or 10 carbon atoms in the aryl group and optionally 1 to 4 carbon atoms in the alkyl moiety, or represents in each case optionally nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, or di-($C_1$–$C_4$-alkyl)-aminosulphonyl-substituted monocyclic or bicyclic heterocyclyl or hetero-cyclylalkyl having in each case up to 10 carbon atoms and up to 4 nitrogen atoms and/or 1 or 2 oxygen or sulphur atoms in the heterocyclyl group and optionally 1 to 4 carbon atoms in the alkyl moiety, $Z^1$ represents C—$R^4$, $Z^2$ represents C–$R^4$, and $Z^3$ represents C—$R^4$.

3. A compound according to claim 1 in which $R^2$ represents nitro, cyano, $SF^5$, fluorine, chlorine, or bromine, or represents in each case optionally cyano-, fluorine-, chlorine-, methoxy-, or ethoxy-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, methylsulphonyloxy, ethylsulphonyloxy, or n- or i-propylsulphonyloxy, $R^3$ represents hydrogen, fluorine, chlorine or bromine, or $R^3$ and $R^2$ together represent in each case optionally fluorine- and/or chlorine-substituted methylenedioxy or ethylenedioxy, $R^4$ represents hydrogen, cyano, carboxyl, carbamoyl, fluorine, chlorine, or bromine or represents optionally cyano-, fluorine-, chlorine-, methoxy-, or ethoxy-substituted methyl, ethyl, or n- or i-propyl, $Q^1$ represents O, $R^5$ represents hydrogen or amino, represents in each case optionally cyano-, fluorine-, chlorine-, methoxy-, or ethoxy-substituted methyl, ethyl, n- or i-propyl, n-, i-, s-, or t-butyl, methylamino, ethylamino, n- or i-propylamino, or n-, i-, s-, or t-butylamino, represents dimethylamino or diethylamino, represents propylideneamino or butylideneamino, represents in each case optionally cyano-, fluorine-, chlorine-, and/or bromine-substituted propenyl, butenyl, propynyl, or butynyl, represents in each case optionally cyano-, fluorine-, chlorine-, bromine-, methyl-, ethyl-, or n- or i-propyl-substituted cyclopropyl, cyclobutyl, cyclopentyl, cyclohexyl, cyclopropylamino, cyclobutylamino, cyclopentylamino, cyclohexylamino, cyclopropylmethyl, cyclob utylmethyl, cyclopentylmethyl, or cyclohexylmethyl, represents in each case optionally nitro-, cyano-, phenyl-, phenoxy-, phenylthio-, fluorine-, chlorine-, bromine-, methyl-, ethyl-, n- or i-propyl-, n-, i-, s-, or t-butyl-, dichloromethyl-, difluoromethyl-, trichloromethyl-, trifluoromethyl-, chloro-difluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoro-methylsulphonyl-, or dimethylaminosulphonyl-substituted phenyl, naphthyl, phenylamino, benzyl, or phenylethyl, or represents in each case optionally cyano-, phenyl-, phenoxy-, phenylthio-, fluorine-, chlorine-, bromine-, methyl-, ethyl-, n- or i-propyl-, n-, i-, s-, or t-butyl-, dichloromethyl-, difluoromethyl-, trichloromethyl-, trifluoromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoro-methylthio-, methylsulphinyl-, ethylsulphinyl-, trifluoromethylsulphinyl-, methylsulphonyl-, ethylsulphonyl-, trifluoromethylsulphonyl-, or dimethyl-aminosulphonyl-substituted heterocyclyl or heterocyclylalkyl selected from the group consisting of furyl, tetrahydrofuryl, benzofuryl, thienyl, benzothienyl, pyrrolyl, benzopyrrolyl, pyrazolyl, benzopyrazolyl, oxazolyl, benzoxazolyl, isoxazolyl, thiazolyl, benzothiazolyl, oxadiazolyl, thiadiazolyl, pyridinyl, quinolinyl, pyrimidinyl, furylmethyl, thienylmethyl, pyrrolylmethyl, pyrazolyl-methyl, oxazolylmethyl, thiazolylmethyl, pyridinylmethyl, and pyrimidinyl-methyl, $R^6$ represents in each case optionally fluorine- and/or chlorine-substituted methyl, ethyl, n- or i-propyl, or n-, i-, s-, or t-butyl, represents in each case optionally fluorine-, chlorine-, and/or bromine-substituted propenyl or butenyl, represents in each case optionally fluorine-, chlorine-, bromine-, methyl-, ethyl-, or n- or i-propyl-substituted cyclopropyl, cyclobutyl, cyclopentyl, cyclohexyl, cyclopropylmethyl, cyclobutylmethyl, cyclopentylmethyl, or cyclohexylmethyl, represents in each case optionally nitro-, cyano-, fluorine-, chlorine-, bromine-, methyl-, ethyl-, n- or i-propyl-, n-, i-, s-, or t-butyl-, dichloromethyl-, difluoromethyl-trichloromethyl-, trifluoromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl-, or dimethyl-aminosulphonyl-substituted phenyl or naphthyl, or represents in each case optionally cyano-, fluorine-, chlorine-, bromine-, methyl-, ethyl-, n- or i-propyl-, n-, i-, s-, or t-butyl-, dichloromethyl-, difluoromethyl-, trichloromethyl-, trifluoromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl-, or dimethylaminosulphonyl-substituted heterocyclyl or heterocyclylalkyl selected from the group consisting of furyl, benzofuryl, thienyl, benzothienyl, pyrrolyl, benzopyrrolyl, pyrazolyl, benzopyrazolyl, oxazolyl, benzoxazolyl, isoxazolyl, thiazolyl, benzothiazolyl, pyridinyl, quinolinyl, pyrimidinyl, furylmethyl, thienylmethyl, pyrrolylmethyl, pyrazolylmethyl, oxazolylmethyl, thiazolylmethyl, pyridinylmethyl, and pyrimidinylmethyl, $Z^1$ represents CH, $Z^2$ represents CH, and $Z^3$ represents CH.

4. A compound according to claim 1 in which $R^2$ represents cyano, fluorine, chlorine, or bromine, or represents in each case optionally fluorine-, chlorine-, methoxy-, or ethoxy-substituted methyl, ethyl, methoxy, ethoxy, methylthio, ethylthio, methylsulphinyl, ethylsulphinyl, methylsulphonyl, ethylsulphonyl, methylsulphonyloxy, or ethylsulphonyloxy, $R^4$ represents hydrogen, cyano, fluorine, chlorine, or bromine, or represents optionally fluorine-, chlorine-, methoxy-, or ethoxy-substituted methyl or ethyl, $R^5$ represents hydrogen or amino, represents in each case optionally cyano-, fluorine-, chlorine-, methoxy-, or ethoxy-substituted methyl, ethyl, n- or i-propyl, methylamino, ethylamino, or n- or i-propylamino, represents dimethylamino, represents in each case optionally fluorine-, chlorine-, and/or bromine-substituted propenyl, butenyl, propynyl, or butynyl, represents in each case optionally fluorine-, chlorine-, bromine-, methyl-, or ethyl-substituted cyclopropyl, cyclopentyl, cyclohexyl, cyclopropylamino, cyclopentylamino, cyclohexylamino, cyclopropylmethyl, cyclopentylmethyl, or cyclohexylmethyl, or represents in each case optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl-, or dimethylaminosulphonyl-substituted phenyl, phenylamino, benzyl, or phenylethyl, $R^6$ represents in each case optionally fluorine- and/or chlorine-substituted methyl, ethyl, n- or i-propyl, or n-, i-, s-, or t-butyl, represents in each case optionally fluorine-, chlorine-, bromine-, methyl-, or ethyl-substituted cyclopropyl, cyclopentyl, or cyclohexyl, or represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl-, or dimethylaminosulphonyl-substituted phenyl.

5. A compound according to claim 1 in which $R^2$ represents trifluoromethyl, and/or $R^4$ represents methyl.

6. A compound according to claim 1 in which $R^1$ represents cyano or one of the groups —CQ$^1$-Q$^2$-R$^5$ or —SO$_2$—R$^6$, $R^2$ represents trifluoromethyl, difluoromethoxy, or trifluoromethoxy, $R^3$ represents hydrogen, fluorine, or chlorine, or R$^3$ in the ortho position and R$^2$ together represent difluoromethylenedioxy or tetrafluoroethylenedioxy, $R^4$ represents hydrogen, fluorine, chlorine, bromine, or methyl, $Q^1$ represents O or S, $Q^2$ represents a single bond or represents O, S, or N—R$^5$, $R^5$ represents hydrogen, represents in each case optionally cyano-, fluorine-, chlorine-, methoxy-, or ethoxy-substituted methyl, ethyl, or n- or i-propyl, represents in each case optionally fluorine-, chlorine-, and/or bromine-substituted propenyl, butenyl, propynyl, or butynyl, represents in each case optionally fluorine-, chlorine-, or methyl-substituted cyclopropyl, cyclopentyl, cyclohexyl, cyclopropylmethyl, cyclopentylmethyl, or cyclohexylmethyl, or represents in each case optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl-, or dimethylaminosulphonyl-substituted phenyl or benzyl, $R^6$ represents in each case optionally fluorine- and/or chlorine-substituted methyl, ethyl, n- or i-propyl, or n-, i-, s-, or t-butyl, represents in each case optionally fluorine-, chlorine-, or methyl-substituted cyclopropyl, cyclopentyl, or cyclohexyl, or represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl-, or dimethyl-aminosulphonyl-substituted phenyl, $Z^1$ represents CH,
$Z^2$ represents CH, and
$Z^3$ represents CH.

7. A process for preparing a substituted iminoazine of the formula (I) according to claim 1 comprising
(a) reacting an iminoazine of the formula (II)

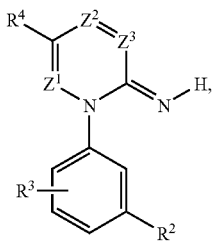
(II)

in which $R^2$, $R^3$, $R^4$, $Z^1$, $Z^2$, and $Z^3$ are each as defined in claim 1, or an acid adduct thereof,
with a compound of the formula (III)

$$X^1—R^1 \qquad (III)$$

in which
$X^1$ represents halogen, —SO$_2$CH$_3$, —O—CO—R$^5$, or —O—SO$_2$—R$^6$, and
$R^1$, $R^5$, and $R^6$ are as defined in claim 1, or
with an iso(thio)cyanate of the formula (IV)

$$Q^1=C=N—R^5 \qquad (IV)$$

in which $Q^1$ and $R^5$ are each as defined in claim 1,
optionally in the presence of a reaction auxiliary and optionally in the presence of a diluent, or
(b) reacting an azinethione of the formula (V)

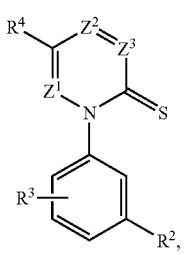
(V)

in which $R^2$, $R^3$, $R^4$, $Z^1$, $Z^2$, and $Z^3$ are each as defined in claim 1,
with a compound of the formula (VI)

$$M^+Cl^-N—SO_2—R^6 \qquad (VI)$$

in which
$R^6$ is as defined in claim 1, and
M represents a metal equivalent,
optionally in the presence of one or more diluents, or
(c) reacting a chloroazinium compound of the formula (VII)

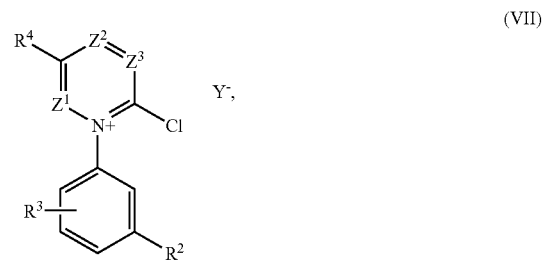
(VII)

in which
$R^2$ $R^3$, $R^4$, $Z^1$, $Z^2$, and $Z^3$ are each as defined in claim 1, and
Y represents Cl, PCl$_4$, POCl$_4$ or PCl$_6$,
with an amino compound of the formula (VIII)

$$H_2N—R^1 \qquad (VIII)$$

in which $R^1$ is as defined in claim 1,
optionally in the presence of a reaction auxiliary and optionally in the presence of a diluent, or
(d) reacting an iminoazine of the formula (II)

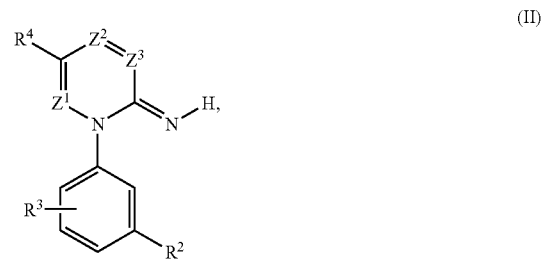
(II)

in which $R^2$, $R^3$, $R^4$, $Z^1$, $Z^2$, and $Z^3$ are each as defined in claim 1, or an acid adduct thereof,
with nitric acid, optionally in the presence of a reaction auxiliary and/or diluent.

8. A method for controlling undesirable vegetation comprising allowing at least one compound according to claim 1 to act on undesirable plants and/or their habitat.

9. An herbicidal composition comprising a compound according to claim 1 and customary extenders and/or surfactants.

10. A process for preparing an herbicidal composition comprising mixing at least one compound according to claim 1 with extenders and/or surfactants.

* * * * *